United States Patent [19]
Heveling et al.

[11] Patent Number: 6,080,865
[45] Date of Patent: Jun. 27, 2000

[54] PIPERIDINOPENTANAMINES, PROCESS FOR PRODUCING THEM AND THEIR USE AS A CATALYST FOR PRODUCING URETHANES

[75] Inventors: Josef Heveling, Naters; Andreas Gerhard, Visp, both of Switzerland

[73] Assignee: Lonza AG, Gampel/Valais, Switzerland

[21] Appl. No.: 08/930,583

[22] PCT Filed: Mar. 19, 1996

[86] PCT No.: PCT/EP96/01179

§ 371 Date: Oct. 20, 1997

§ 102(e) Date: Oct. 20, 1997

[87] PCT Pub. No.: WO96/33986

PCT Pub. Date: Oct. 31, 1996

[30] Foreign Application Priority Data

Apr. 26, 1995 [CH] Switzerland ............... 1190/95

[51] Int. Cl.$^7$ ................................. C07D 211/26
[52] U.S. Cl. ............................................. 546/246
[58] Field of Search ............................. 546/246

[56] References Cited

U.S. PATENT DOCUMENTS

| | | | |
|---|---|---|---|
| 2,949,431 | 8/1960 | Britain | 260/2.5 |
| 4,256,800 | 3/1981 | Stockhausen et al. | 546/246 |
| 4,992,150 | 2/1991 | Igarashi et al. | 546/246 |
| 5,059,391 | 10/1991 | Botta et al. | 546/246 |
| 5,134,217 | 7/1992 | Weider et al. | 528/53 |
| 5,268,470 | 12/1993 | Puckett et al. | 540/596 |

FOREIGN PATENT DOCUMENTS

| | | |
|---|---|---|
| 2155472 | 10/1996 | Canada . |
| 0 495 249 A1 | 7/1992 | European Pat. Off. . |
| 0 696 580 A2 | 2/1996 | European Pat. Off. . |
| 2085965 | 12/1971 | France . |
| 4033632 A1 | 5/1991 | Germany . |
| 1338275 | 11/1973 | United Kingdom . |

OTHER PUBLICATIONS

International Publication No. WO 90/00546, published Jan. 25, 1990.

Chemical Abstracts, vol. 90, No. 17, (Apr. 23, 1979), 137153.

Katsamberis et al., J. Applied Polymer Science, vol. 41, No. 9/10, (1990), pp. 2059 to 2065.

*Primary Examiner*—John Kight
*Assistant Examiner*—Raymond Covington
*Attorney, Agent, or Firm*—Fisher, Christen & Sabol

[57] ABSTRACT

Methyl-5-(3-methyl piperidino)pentanamines of general formula

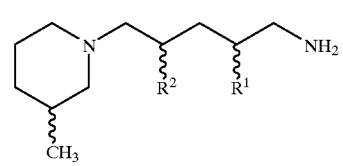

in which one of the two radicals $R^1$, $R^2$ is hydrogen and the other methyl, are produced by two-stage hydrogenation from 2-methyl glutaronitrile. The compounds are suitable as catalysts in the production of polyurethanes.

20 Claims, No Drawings

PIPERIDINOPENTANAMINES, PROCESS FOR PRODUCING THEM AND THEIR USE AS A CATALYST FOR PRODUCING URETHANES

This application is a 371 of PCT/EP96/61179 filed Mar. 19, 1996.

BACKGROUND OF THE INVENTION

1. Field of the Invention

The present invention relates to new piperidinopentanamines, both individually and as a mixture, namely 2-methyl-5-(3-methylpiperidino)pentanamine and the isomeric 4-methyl-5-(3-methylpiperidino)pentanamine, which can be represented by the common formula

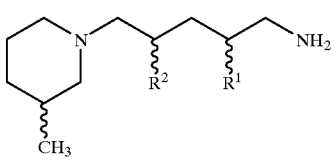

In this formula, in both cases, one of the two radicals $R^1$ and $R^2$ is hydrogen and the other is methyl. In the case of 2-methyl-5-(3-methylpiperidino)pentanamine (Ia), $R^1$=methyl and $R^2$=H, in the case of 4-methyl-5-(3-methylpiperidino)pentanamine (Ib), $R^1$=H and $R^1$=methyl. Each of the two compounds can exist in four different stereoisomeric forms (two diastereomeric pairs). Here and in the following, the formulae and the associated names of compounds represent all possible stereoisomers in each case.

The invention further relates to a process for preparing the abovementioned compounds from 2-methylglutaronitrile and the use of the compounds as catalysts for producing polyurethanes from polyisocyanates and polyols.

2. Background Art

Polyurethanes are customarily produced using nitrogen bases, in particular tertiary amines such as 1,4-diazabicyclo[2.2.2]octane (DABCO®), cyclic amidines such as 1,8-diazabicyclo[5.4.0]undec-7-ene ("DBU") or guanidine derivatives such as tetramethylguanidine as catalysts. Decisive for the suitability as catalyst are, inter alia, the basicity, solubility behavior and volatility. While the basicity primarily determines the catalytic effectiveness, solubility behavior and volatility are likewise important for the processing properties. For example, volatility which is too high can lead to irritation or danger to people as a result of liberation into the atmosphere during the production of the polyurethanes or during their use.

BROAD DESCRIPTION OF THE INVENTION

It is an object of the present invention to provide new amines which are suitable as catalysts for producing polyurethanes, have favourable use properties and can be prepared simply and inexpensively.

According to the invention, object is achieved by means of the piperidinopentanamines of the invention and preparation process of the invention.

It has been found that the 2-methylglutaronitrile formed as by-product in adiponitrile production can be reacted with hydrogen in the presence of a catalyst in one stage to give, apart from other products, a mixture of the two isomeric methyl-5-(3-methylpiperidino)pentanonitriles of the general formula

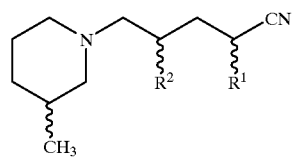

where one of the two radicals $R^1,R^2$ is hydrogen and the other is methyl, which can be hydrogenated in a second stage in the presence of a second catalyst to give the mixture of the two isomeric methyl-5-(3-methylpiperidino)pentanamines Ia and Ib.

The isomer mixture Ia/Ib can, if desired, be separated by distillation or chromatography into the two structural isomers Ia and Ib, but is preferably used as such.

The catalyst used for the first stage is preferably a supported palladium catalyst, particular preference being given to palladium on aluminium oxide.

The reaction of the 2-methylglutaronitrile with hydrogen is preferably carried out at a temperature of from 100° to 250° C. and a pressure of from 20 to 70 bar.

It has been found to be advantageous to add some 3-methylpiperidine to the 2-methylglutaronitrile. The 3-methylpiperidine is preferably added in an amount of from 1 to 5 mol per 1 mol of 2-methylglutaronitrile. This significantly increases the selectivity of the reaction. 3-Methylpiperidine can be prepared by known methods, likewise from 2-methylglutaronitrile (WO 90/00 546).

The reaction of the 2-methylglutaronitrile with hydrogen is preferably carried out continuously in a fixed-bed reactor.

The hydrogenation of the methyl-5-(3-methylpiperidino)pentanonitriles II to give the methyl-5-(3-methylpiperidino)pentanamines Ia/Ib is advantageously carried out in the presence of ammonia so as to suppress undesired secondary reactions.

Catalysts which can be used for this second stage are essentially all catalysts which are suitable for the hydrogenation of nitrites to amines, i.e. for example palladium, platinum, rhodium, cobalt, nickel or nickel boride.

The catalyst used for the second stage is preferably a supported rhodium catalyst, particular preference being given to rhodium on activated carbon.

The hydrogenation of the methyl-5-(3-methyl-piperidino)pentanonitriles II over a supported rhodium catalyst is preferably carried out at a temperature of from 50 to 100° C. and a pressure of from 1 to 50 bar.

Solvents which can be used for the second stage are the solvents customary for the hydrogenation of nitriles to amines. Preference is given to using alcohols such as ethanol or tert-butyl alcohol.

The methyl-5-(3-methylpiperidino)pentanamines Ia/Ib of the invention can, as already mentioned in the introduction, be used as catalysts for producing polyurethanes.

DETAILED DESCRIPTION OF THE INVENTION

The following examples illustrate the preparation and use of the compounds of the invention.

EXAMPLES

Example 1

A reactor (13 mm Ø) was charged with 3 g of Pd/Al$_2$O$_3$ catalyst (1% Pd, particle size 0.315–1.0 mm) The reactor was heated to the reaction temperature of 150° C. in a stream of hydrogen (120 ml/min, based on atmospheric pressure) at 50 bar. A mixture of 3-methylpiperidine and 2-methylglutaronitrile in a molar ratio of 2:1 was then metered into the hydrogen. The throughput was 2.1 g of starting material per g of catalyst and hour. The product mixture after leaving the reactor and separating off the hydrogen contained, according to GC, 44.8% of 2(4)-methyl-5-(3-methylpiperidino)pentanonitrile (isomer mixture), 30.2% of 3-methylpiperidine and 24.4% of 1,5-bis(3-methylpiperidino)-2-methylpentane and 0.6% of unidentified products.

The mixture was collected over a reaction time of 260 hours and subsequently fractionated under reduced pressure. At 87° C./2.5 mbar, the methyl-5-(3-methylpiperidino) pentanonitrile distilled over in a purity of 99.5% (GC). According to NMR analysis, this was a mixture of 85% of 2-methyl compound and 15% of 4-methyl compound.

| Analytical data: | |
|---|---|
| $C_{12}H_{22}N_2$ calculated: | C 74.2 H 11.4 N 14.4 |
| found: | C 74.2 H 11.6 N 14.9 |
| $^1$H NMR (CDCl$_3$, 400 MHz) δ: (main component) | 1.40–2.85 (m, 16H, CH + CH$_2$); 1.32 (d, 3H, CH$_3$—CH—CN); 0.86 (d, 3H, ring CH$_3$). |
| $^{13}$C NMR (CDCl$_3$, 100 MHz) δ: (main component) | 123.01 (s); 62.20 (t); 58.28 (t); 54.12 (t); 33.13 (t); 32.23 (t); 31.19 (d); 25.62 (t). |

Example 2

The procedure of Example 1 was repeated, but the reaction temperature was only 125° C.

The product mixture contained about 50% of 2-methyl-5-(3-methylpiperdino)pentanonitrile, 8% of 4-methyl-5-(3-methylpiperidino)pentanonitrile, 32% of 3-methylpiperidine, 6% of 1,5-bis(3-methylpiperidino)-2-methylpentane, 1% of 2-methylglutaronitrile and 3% of unidentified products.

The mixture was collected over a reaction time of 284 hours and subsequently fractionated under reduced pressure. At 87° C./2.5 mbar, the methyl-5-(3-methylpiperidino) pentanonitrile distilled over in a purity of 99.3% (GC). According to NMR analysis, this was a mixture of 86% of the 2-methyl compound and 14% of the 4-methyl compound.

Example 3

A reactor (13 mm Ø) was charged with 3 g of a Pd/MgCl$_2$/Al$_2$O$_3$ catalyst (1% Pd, 1.2% Mg, particle size 0.315–1.0 mm). The reactor was heated to the reaction temperature of 160° C. in a stream of hydrogen (120 ml/min, based on atmospheric pressure) at 50 bar. 99.8% strength 2-methylglutaronitrile was then metered into the hydrogen. The throughput was 2.1 g of starting material per g of catalyst and hour. According to GC, the product stream contained 25.8% of 2(4)-methyl-5-(3-methylpiperidino)-pentanonitrile (isomer mixture), 52.1% of 1,5-bis(3-methylpiperidino)-2-methylpentane, 3.7% of 3-methylpiperidine and 18.4% of unidentified products.

The selectivity of the reaction to give the desired nitriles was significantly lower than in Examples 1 and 2 (with addition of 3-methylpiperidine).

Example 4

Ammonia was passed into 100 g of dry tert-butyl alcohol while cooling until a concentration of 13.7% of NH$_3$ had been reached. A 100 ml autoclave having a magnetically driven stirrer was flushed with nitrogen and precooled. 30 g of the solution of ammonia in tert-butyl alcohol, 4 g of rhodium/activated carbon (5% Rh) and 30 g of the mixture of methyl-5-(3-methylpiperidino)pentanonitriles from Example 1 were then introduced. The autoclave was closed and heated while stirring. It was pressurized with hydrogen to 10 bar at room temperature, then the temperature was increased further to 50° C. According to GC, after 6 hours a conversion of 99.2% and a yield of 87.3% had been achieved.

The reaction mixture was distilled under reduced pressure, giving the isomer mixture 2(4)-methyl-5-(3-methylpiperidino)pentanamine at 104° C./3 mbar in a purity of 99.5%. According to GC, the mixture contained the 2-methyl compound and the 4-methyl compound in a ratio of 2.6:1.

| Analytical data: | |
|---|---|
| $C_{12}H_{26}N_2$ calculated: | C 72.7 H 13.2 N 14.1 |
| found: | C 72.9 H 13.1 N 14.6 |
| $^1$H NMR (CDCl$_3$, 400 MHz) δ = | 0.6–0.8 (CH$_3$, 1 methylene H); 1.0–1.25 (NH$_2$, 1 methylene H); 1.30–1.85; 2.05; 2.27; 2.55; 2.65–2.80. |

Owing to the presence of a number of diastereomeric forms, the NMR spectra are very complex.

Examples 5–8

The isomer mixture of 2-methyl-5- (3-methylpiperidino) pentanamine/4-methyl-5- (3-methylpiperidino) pentanamine (2.6:1) from Example 4 was used as polyurethane catalyst:

Abbreviations:

VL: Desmodur® VL from Bayer, aromatic diisocyanate containing about 32% of NCO

D550U: Desmophen® 550U, polypropylene glycol from Bayer, trifunctional containing 10.5% of OH DBU: diazabicyclo[5.4.0]undec-7-ene MMPPA: mixture of 2-methyl- and 4-methyl-5-(3-methylpiperidino)pentanamine (2.6:1)

DBU was used as comparative catalyst. Desmophen® was initially charged together with the amine (DBU or MMPPA) and mixed well. This gave a solution. In Examples 7 and 8, water was additionally added. This gave an emulsion/solution. A weighed amount of isocyanate (VL) was added at a point in time t=0 with vigorous stirring. The points in time at which the solution was no longer turbid, at which significant warming could be detected, at which the mixture became solid were noted.

The results (MMPPA in comparison with DBU) are shown in Table 1 below:

TABLE 1

| Ex. No. | t [s] no longer turbid | t [s] no war-ming | t [s] solid | VL [g] | D550U [g] | DBU [g] | MMPPA [g] | H₂O [g] | Vol. [ml] | Comments (colour etc.) |
|---|---|---|---|---|---|---|---|---|---|---|
| 5 | 550 | 360 | 820 | 50.0 | 55.0 | 0.1 | — | — |  | brown/ochre, rigid |
| 6 | 295 | 145 | 550 | 50.0 | 55.0 | — | 0.1 | — |  | ochre, rigid |
| 7 | 200 | 180 | 1180 | 50.0 | 45.0 | 0.1 | — | 0.5 | 400 | ochre, rigid foam |
| 8 | 175 | 150 | 960 | 50.0 | 45.0 | — | 0.1 | 0.5 | 300 | ochre, rigid |

Examples 9–12

The polymer from Examples 5 and 6 was changed into fine flakes and in each case 4 g of these were slurried in 45 g of ethanol and agitated daily. GC was used to determine the amount of catalyst which had been leached from the polymer after one day, after one week and after three weeks. The results (MMPPA in comparison with DBU) are shown in Table 2 below. It was found that, in contrast to DBU, the new catalyst was not eluted. The experiment was then repeated using a larger amount of catalyst (Examples 11 and 12). After one day, MMPPA could now be detected in the solution, but the amount was significantly less than in the corresponding comparative experiment using DBU and showed virtually no increase over the next 3 weeks.

TABLE 2

| Ex. No. | Catalyst | Amount of cat. [g] | 1 day [GC area] | 1 week [GC area] | 3 weeks [GC area] |
|---|---|---|---|---|---|
| 9 | DBU | 0.1 | 3520 | 3580 | 7080 |
| 10 | MMPPA | 0.1 | 0 | 0 | 0 |
| 11 | DBU | 0.5 | 15800 | 21900 | 28200 |
| 12 | MMPPA | 0.5 | 580/1290* | 475/1350* | 590/1460* |

*The first number relates to the 4-methyl compound, the second to the 2-methyl compound

What is claimed is:

1. A methyl-5-(3-methylpiperidino) pentanamine of formula:

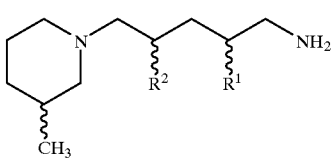

I wherein one of the two radicals R¹ and R² is hydrogen and the other is methyl, or a mixture of two of such methyl-5-(3-methylpiperidino)pentanamines.

2. 2-Methyl-5-(3-methylpiperidino)pentanamine of the formula,

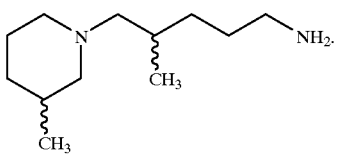

Ia 3. 4-Methyl-5-(3-methylpiperidino)pentanamine of the formula,

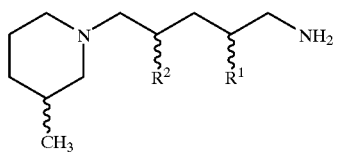

Ib

4. Process for preparing a methyl-5-(3-methylpiperidino) pentanamine of the formula:

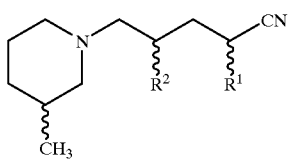

I wherein one of the two radical R¹ and R² is hydrogen and the other is methyl, or a mixture of two of such methyl-5-(3-methylpiperidino)pentanamines, characterized in that, in a first stage, 2-methylglutaronitrile, with or without addition of 3-methylpiperidine, is reacted with hydrogen in the presence of a first catalyst to give a mixture of the isomeric methyl-5-(3-methylpiperidino)pentanonitriles of formula:

II wherein R¹ and R² are as defined above, which is, in a second stage, hydrogenated in the presence of a second catalyst to give a mixture of the isomeric methyl-5-(3- methylpiperidino)pentanamines (Ia/Ib) and, if desired, this is separated into the two structural isomers.

5. Process according to claim 4, characterized in that the first catalyst used is a supported palladium catalyst.

6. Process according to claim 5, characterized in that the supported palladium catalyst used is palladium on aluminium oxide.

7. Process according to claim 6, characterized in that the reaction of the 2-methylglutaronitrile with hydrogen is carried out at a temperature of from 100° to 250° C. and a pressure of from 20 to 70 bar.

8. Process according to claim 7, characterized in that 1 to 5 times the molar amount of 3-methylpiperidine is added to the 2-methylglutaronitrile.

9. Process according to claim 8, characterized in that the reaction of the 2-methylglutaronitrile with hydrogen is carried out continuously in a fixed-bed reactor.

10. Process according to claim 9, characterized in that the hydrogenation of the methyl-5-(3-methylpiperidino) pentanonitriles (II) is carried out in the presence of ammonia.

11. Process according to claim 10, characterized in that the second catalyst used is a supported rhodium catalyst.

12. Process according to claim 11, characterized in that the supported rhodium catalyst used is rhodium on activated carbon.

13. Process according to claim 11, characterized in that the hydrogenation of the methyl-5-(3-methylpiperidino) pentanonitriles is carried out at a temperature of from 5 to 100° C. and a pressure of from 1 to 50 bar.

14. Process comprising using a methyl-5-(3-methylpiperidino)pentanamine of the formula:

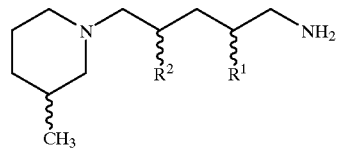

wherein one of the two radical $R^1$ and $R^2$ is hydrogen and the other is methyl, or a mixture of two or more of such methyl-5-(3-methylpiperidino)pentanamines, as a catalyst for preparing a polyurethane.

15. Process according to claim 5, characterized in that the reaction of the 2-methylglutaronitrile with hydrogen is carried out at a temperature of from 100° to 250° C. and a pressure of from 20 to 70 bar.

16. Process according to claim 4, characterized in that 1 to 5 times the molar amount of 3-methylpiperidine is added to the 2-methylglutaronitrile.

17. Process according to claim 4, characterized in that the reaction of the 2-methylglutaronitrile with hydrogen is carried out continuously in a fixed-bed reactor.

18. Process according to claim 4, characterized in that the hydrogenation of the methyl-5-(3-methylpiperidino) pentanonitriles (II) is carried out in the presence of ammonia.

19. Process according to claim 4, characterized in that the second catalyst used is a supported rhodium catalyst.

20. Process according to claim 11, characterized in that the hydrogenation of the methyl-5-(3-methylpiperidino) pentanonitriles is carried out at a temperature of from 5° to 100° C. and a pressure of from 1 to 50 bar.

* * * * *